(12) United States Patent
Hooftman et al.

(10) Patent No.: US 12,070,626 B2
(45) Date of Patent: Aug. 27, 2024

(54) PROTON THERAPY GANTRY

(71) Applicant: ITREC B.V., Schiedam (NL)

(72) Inventors: Maarten Hugo Hooftman, Schiedam (NL); Joop Roodenburg, Schiedam (NL)

(73) Assignee: ITREC B.V., Schiedam (NL)

( * ) Notice: Subject to any disclaimer, the term of this patent is extended or adjusted under 35 U.S.C. 154(b) by 76 days.

(21) Appl. No.: 17/265,412

(22) PCT Filed: Jul. 25, 2019

(86) PCT No.: PCT/NL2019/050490
§ 371 (c)(1),
(2) Date: Feb. 2, 2021

(87) PCT Pub. No.: WO2020/027656
PCT Pub. Date: Feb. 6, 2020

(65) Prior Publication Data
US 2021/0299479 A1    Sep. 30, 2021

(30) Foreign Application Priority Data

Aug. 3, 2018  (NL) .................................. 2021421

(51) Int. Cl.
*A61N 5/10*    (2006.01)
(52) U.S. Cl.
CPC ......... *A61N 5/1079* (2013.01); *A61N 5/1081* (2013.01); *A61N 2005/1087* (2013.01)

(58) Field of Classification Search
CPC ................ A61N 5/1079; A61N 5/1081; A61N 2005/1087
See application file for complete search history.

(56) References Cited

U.S. PATENT DOCUMENTS

| | | | |
|---|---|---|---|
| 4,914,682 A * | 4/1990 | Blumenthal | A61B 6/0487 378/208 |
| 5,349,198 A | 9/1994 | Takanaka | |
| 5,993,373 A | 11/1999 | Nonaka et al. | |

(Continued)

FOREIGN PATENT DOCUMENTS

| | | |
|---|---|---|
| CN | 106492356 B | 2/2018 |
| JP | 05-161720 A | 6/1993 |

(Continued)

OTHER PUBLICATIONS

Dutch Search Report, issued in Application No. 2021421, dated Apr. 10, 2019.

(Continued)

*Primary Examiner* — Marcus H Taningco
(74) *Attorney, Agent, or Firm* — Birch, Stewart, Kolasch & Birch, LLP

(57) ABSTRACT

A radiation facility includes a radiation assembly, preferably for irradiating a patient and, more particularly, to a novel and highly-effective method and apparatus for radiation therapy for patients. The radiation assembly includes a radiation device and a moveable radiation device gantry whereupon the radiation device is mounted. The radiation device includes an accelerator and a projector for irradiating patients. The radiation assembly is movable relative to multiple patient preparation rooms.

17 Claims, 8 Drawing Sheets

(56) References Cited

U.S. PATENT DOCUMENTS

| | | | |
|---|---|---|---|
| 7,531,818 B2* | 5/2009 | Brahme | A61N 5/10 600/436 |
| 8,536,547 B2 | 9/2013 | Maurer, Jr. et al. | |
| 11,446,521 B2 | 9/2022 | Paul | |
| 2003/0141460 A1 | 7/2003 | Kraft | |
| 2006/0260050 A1 | 11/2006 | Manzione | |
| 2007/0094797 A1* | 5/2007 | Bartels | A61B 6/04 5/601 |
| 2008/0093567 A1 | 4/2008 | Gall | |
| 2012/0228522 A1 | 9/2012 | Sasai | |
| 2013/0066134 A1* | 3/2013 | Carol | A61N 5/10 378/65 |
| 2016/0107001 A1 | 4/2016 | Ishiyama et al. | |
| 2018/0014797 A1 | 1/2018 | Keibel | |
| 2018/0104513 A1 | 4/2018 | Sliski | |
| 2018/0264290 A1* | 9/2018 | Hassan | A61N 5/1081 |
| 2020/0346040 A1* | 11/2020 | Paul | E04H 3/08 |

FOREIGN PATENT DOCUMENTS

| | | |
|---|---|---|
| JP | 2012-187269 A | 10/2012 |
| JP | 2016-077763 A | 5/2016 |
| JP | 2016-147116 A | 8/2016 |

OTHER PUBLICATIONS

International Search Report, issued in PCT/NL2019/050490, dated Oct. 17, 2019.

Written Opinion of the International Searching Authority, issued in PCT/NL2019/050490, dated Oct. 17, 2019.

English translation of Japanese Office Action, issued in 2021-505831, dated Aug. 29, 2022.

* cited by examiner

PROTON THERAPY GANTRY

BACKGROUND OF THE INVENTION

Field of the Invention

This invention relates to a radiation assembly, to a radiation facility comprising such a radiation assembly, preferably for irradiating a patient and, more particularly, to a novel and highly-effective method and apparatus for radiation therapy for patients.

Description of the Prior Art

Effective treatment of patients, in particular when using proton radiation, requires a short and direct radiation beam trajectory between the accelerator and the patient. It also benefits from the ability to provide an optimal angle of incidence for the radiation beam, more in particular to allow for an angle of incidence that ensures that a minimum of healthy tissue is irradiated and that vital organs are evaded. This is furthermore relevant because radiation therapy typically requires radiating a target form different angles.

A difficulty in achieving these objects is the size of a typical accelerator. Even though for particular treatment compact accelerators are available, these are of a considerable size. For practical reasons, the accelerator is often located in a room separate from the room in which the patient is treated. In such cases the radiation beam is guided by magnets through the projector from which the beam is projected onto the patient.

For example from U.S. Pat. No. 5,349,198 it is known to guide a beam from an accelerator to different treatment rooms.

It is also known from the prior art to mount an accelerator on a gantry. This allows for locating the accelerator in the vicinity of the patient, and thus for a short beam trajectory between accelerator and patient. It also allows for positioning the accelerator at different angles relative to the patient. Such a gantry is for example known from US2008093567, which is incorporated by reference herein.

However, the size and weight of even compact accelerators are such that these gantries are too large to be mounted in a patient treatment room. To provide the patient with a feeling of comfort and safety, these gantries are mounted outside a patient treatment room. The patient treatment room is build such that it extends into the centre of the gantry, and only the projector enters the room. This configuration limits the range of movement available to the gantry. Typically, the trajectory of movement available to the gantry is in the range of 180 degrees up to about 330 degrees.

It should furthermore be noted that these kind of radiation assemblies due to their size and complexity are costly.

OBJECTS AND SUMMARY OF THE INVENTION

It is an object of the invention to provide an alternative radiation assembly, more in particular to provide an improved radiation assembly. It is a further object of the invention to obviate the problems described hereinabove and in particular to provide a radiation assembly with an improved range of movement. It is yet a further object of the invention to provide a radiation assembly that allows for a more efficient use.

The invention therefore provides a radiation assembly according to claim 1. The invention furthermore provides a radiation facility comprising such a radiation assembly and a method for using such a radiation assembly.

A radiation assembly, preferably a proton radiation assembly, according to the invention comprises:
- a radiation device, preferably a proton radiation treatment device, wherein the treatment device comprises an accelerator, preferably a proton accelerator, and a radiation projector;
- a radiation device gantry, wherein the gantry moveable supports the accelerator and projector, such that the accelerator and the projector can in unison be rotated about a horizontal patient treatment axis,
- wherein the gantry provides a range of movement of the radiation device that defines a cylindrical treatment space, extending between a first end and a second opposite end, which cylindrical treatment space has the patient treatment axis at its's centre;
- wherein the gantry comprises a first slew bearing and a second slew bearing to moveably support the treatment device, which slew bearings each have a central rotational axis that is aligned with the patient treatment axis, and
- wherein the first slew bearing has a central opening that defines a treatment space entry port for moving a patient into and out of the treatment space.

The radiation assembly comprises a radiation device, preferably a proton radiation treatment device, supported by a radiation device gantry. The treatment device comprises an accelerator and a radiation projector. The radiation device gantry comprises a first slew bearing and a second slew bearing to moveably support the treatment device, which slew bearings each have a central rotational axis that is aligned with a patient treatment axis.

In an embodiment, the accelerator may be any suitable conventional particle accelerator, for example a linear accelerator, a cyclotron, a synchro-cyclotron, a synchrotron, or a laser based accelerator, and produce a radiation beam for use in patient treatments, e.g. tumor radiation therapy. The radiation beam typically comprises ionizing radiation. The nature of the radiation beam depends on the radiation source with which the particle accelerator is used.

In preferred embodiments, the radiation source comprises a source of protons. As such the radiation beam comprises a proton beam and the system 10 may be described as a proton radiation treatment device. Alternatively, the radiation source may comprise other suitable particles, especially but not exclusively charged particles, for example ions (e.g. Carbon ions, Helium ions or Neon ions), atoms, photons or other sub-atomic particles such as electrons, alpha particles, beta particles, negative pi mesons or neutrons. Hence, in alternative embodiments the radiation beam may comprise, for example, an ion beam, electron beam (especially a relativistic electron beam), a neutron beam or X-ray beam. The radiation source may be incorporated into the particle accelerator or connected to it in any convenient conventional manner.

In an embodiment, the treatment device comprises a neutron beam irradiation system including: an accelerator which accelerates charged particles along an orbit, thereby emitting a charged particle beam; a neutron beam generation section which is irradiated with the charged particle beam emitted from the accelerator, thereby generating a neutron beam; and an irradiation section that can irradiate the neutron beam generated in the neutron beam generation section, towards an irradiated body. Typically, a shielding body which is provided that shields radiation that is radiated from a side of the accelerator.

The radiation projector is configured for delivering the radiation beam to the radiation target, i.e. a patient. The projector may be configured to bend, scan, focus or otherwise manipulate the radiation beam at the point of delivery, and to this end may include one or more bending, scanning and/or focusing magnets (and/or other beam forming and/or beam manipulating and/or energy selection components as required) for energy selection, bending, scanning and/or focusing the radiation beam at the point of delivery as required. Optionally, the projector may be extendible in its longitudinal direction. The projector may be conventional. In a preferred embodiment, the projector is fixed with respect to the particle accelerator so that it moves with the particle accelerator. In a further preferred embodiment there is no beam transport system between the particle accelerator and the projector, in particular no beam transport system that bends the radiation beam between the particle accelerator and the projector. This simplifies the treatment device, reducing cost and increasing reliability.

An example of a proton radiation treatment device that is suitable for use in the invention is the Mevion s250 which is commercially available and compact enough to be mounted on the radiation device gantry of the invention.

It is noted that these kind of radiation devices, including the radiation source, may have a weight in the range of 11 ton up to 100 ton.

According to the invention, at least one of the bearings has a central opening that defines a treatment space entry port for moving a patient into and out of the treatment space at the centre of the gantry, more allows for introducing a patient on the patient treatment axis, i.e. the axis of rotation of the gantry.

Providing the entry port to the treatment space on the axis of rotation of the gantry allows for an unobstructed range of movement of the gantry, more in particular allows for the treatment device to be pivoted about the patient treatment axis over an angle of 360 degrees or more.

Furthermore, it allows for supporting the patient during treatment on an extended table, which extended table has a base mounted outside the treatment space and an arm that extends into the treatment space to position a table top supporting the patient relative to the projector.

A patient treatment room, that encloses the patient treatment space at the centre of the gantry, can be provided without obstructing the range of movement of the gantry, more in particular of the radiation device supported by the gantry.

A radiation assembly according to the invention furthermore allows for an efficient use of the radiation device. More in particular, the entry to the treatment device via the bearing of the gantry provides a compact configuration of the gantry and the treatment device enclosed by the gantry. It allows for moving the gantry perpendicular to the patient treatment axis, and thus moving the entry port perpendicular to the direction of entry. The gantry can therefore be moved along a linear trajectory between a first treatment position, in which the entry port to the treatment space is aligned with the treatment space entry port of a first patient treatment room, and a second treatment position, in which the entry port to the treatment space is aligned with the treatment space entry port of a second patient treatment room.

There is no need for the gantry to be moved in alternate directions or for the patient preparation rooms to be moved relative to the gantry.

Thus, the invention allows for preparing a second patient, in a second preparation room, while a first patient is being treated. Once the first patient has exited the treatment space and is back into the first preparation room, the gantry is moved to enable the second patient to enter the treatment space.

It should be noted that preparing the patient prior to treatment, and the process following the treatment, are time consuming. This is in particular the case with radiation therapy, which involves precisely mounting a patient on a support table, and removing a weakened patient from that table after the treatment.

It therefore saves time to move the gantry to the second preparation. Waiting until the first treatment room is vacated and subsequently preparing the second patient in that preparation room takes up significantly more time than moving a gantry using a manipulator according to the invention.

It should furthermore be noted that by moving the gantry relative to the preparation rooms instead of moving preparation rooms relative to the gantry, the patients move from a stationary preparation room into a stationary treatment space. Moving a preparation room with a patient inside it may cause negative experience by the patient. Furthermore, providing multiple moveable preparation rooms requires a complicated interface between the stationary section of the facility and the preparation rooms.

A radiation treatment assembly according to the invention thus allows for a more efficient use of the radiation treatment device without negatively influencing the experience of the therapy by the patient, which for example could be caused by a more rushed preparation or the use of moving treatment rooms or entryways.

According to a further aspect, the invention provides a radiation facility comprising multiple patient preparation rooms and a gantry manipulator configured to positon the radiation assembly, comprising the radiation device and the radiation device gantry, in a treatment position relative to each of the multiple patient preparation rooms, in which treatment position, the treatment space entry port of the gantry is aligned with the patient transfer opening.

In an embodiment the gantry comprises a, preferably cylindrically shaped, treatment housing, that at least partially encloses the treatment space. The treatment housing is at opposite ends supported by the first slew bearing and the second slew bearing. The treatment device is mounted on the treatment housing, such that by rotating the treatment housing about the treatment axis, the treatment device is rotated about the treatment axis.

The housing has as an advantage that it prevents the patient in the treatment space from observing the radiation device and/or the gantry and thus having a more relaxed treatment experience.

In embodiments the gantry comprises a treatment floor and optionally a treatment chamber, located inside the, preferably cylindrical, treatment housing. The treatment floor is moveable supported relative to the treatment housing, preferably by two or more slew bearings, such that the treatment floor, and optionally the floor of the treatment chamber (inner treatment chamber), does not rotate with the treatment housing. In other words, the treatment floor stays level while the outer treatment housing is rotated about the treatment axis.

Preferably, the treatment floor is a two part floor, the first part of the floor and the second part of the floor being separated by a projector passage, to allow for the radiation projector to be rotated below a patient that is supported on or above the floor. The radiation projector can be moved through the projector passage when rotating the treatment device or the treatment housing, relative about the treatment axis and thus about the floor.

The treatment floor can be used by medical personal while the patient is supported in the treatment room to approach the supported patient. Furthermore the treatment floor can support other equipment which preferably may not rotate around the central rotational axis during treatment. This may include supporting a patient support on which the patient is supported during treatment.

It might also be advantageous for the patient to have a fixed frame while being irradiated. Said floor and chamber provide such a fixed frame preventing the patient from experiencing possible discomfort from seeing the rotatable treatment housing.

In embodiments the treatment device is furthermore supported such that it can be moved in a direction perpendicular to the patient treatment axis, i.e. towards and away from the patient treatment axis.

Moving the treatment device perpendicular to the patient treatment axis improves the functionality of the radiation assembly. The treatment device in this embodiment can be moved in a radial direction with respect to the patient giving a greater area that can be irradiated while keeping the patient stationary lessening potential discomfort for the patient.

Moving the treatment device perpendicular to the patient treatment axis away from the treatment axis may also help create space for moving the patient into treatment position. The treatment device may be moved into treatment position once the patient is ready for treatment.

In embodiments the treatment device is furthermore supported such that it can be pivoted, relative to an axis extending perpendicular to the patient treatment axis.

Pivoting the treatment device relative to the axis extending perpendicular to the patient treatment axis enables adjustment of the angle of the projector relative to the working axis. This increases the functionality of the treatment device by increasing the area that can be irradiated while keeping the patient stationary.

In embodiments the treatment space entry port is large enough for a person to walk through the entry port into and out of the treatment space. This allows for easy access to the treatment space should someone have to enter or exit the treatment space, for instance to comfort the patient or to allow for extra treatment or to do maintenance.

In embodiments the treatment space is large enough for a lying patient to be supported in the treatment space perpendicular to the patient treatment axis. In these embodiments, if the patient is supported perpendicular to the patient treatment axis, the radiation device may be rotated around a longitudinal direction of the patient. This increases the functionality of the radiation assembly as patients may be irradiated from more angles.

In embodiments the second slew bearing has a central opening that defines a second treatment space entry port for moving a patient into and out of the treatment space.

Advantageously, this allows for preparing a second patient in a separate room while a first patient is irradiated. Said second patient can be moved through the second slew bearing when the first patient has been irradiated and moved out of the treatment space through the first slew bearing. Hence, patients may be prepared comfortable while increasing the efficiency of the radiation assembly.

Additionally, the second entry port may, for example, be used by medical personal to move equipment in and out of the treatment room.

In embodiments the gantry furthermore supports a treatment device counterweight, which preferable has a weight similar to the treatment device. The treatment device counterweight is supported diametrically opposite to the treatment device, relative to the treatment axis.

A radiation assembly equipped with a treatment device counterweight has a better weight distribution and allows for easier rotation of the radiation device. It may also give a more stable overall structure to the radiation assembly.

In embodiments the counterweight is a second treatment device, for example a medical imaging device. This has as an advantage that the radiation assembly can be used for more diverse purposes. For instance, using a proton accelerator for irradiating a patient and a medical imaging device for medical imaging to check if the irradiating is successful or done to the right area.

In embodiments, the radiation assembly comprises at least one patient support, preferably a patient support table, for supporting a patient, which can be mounted in the treatment space or supported by the gantry. Preferably the patient support can be used for positioning the patient relative to the radiation device, in particular relative to the projector of the radiation device.

The patient support may, for instance, be a bed mounted on a movable support for positioning the patient relative to the radiation projector. The patient support may be mounted on the treatment floor in the radiation assembly or it may be mounted outside of the radiation gantry or in any other suitable place.

In embodiments, the patient support is configured to move the patient into and out of the patient treatment device so that patient can be positioned and preferably secured on the support outside the treatment space and subsequently be moved into the treatment space to be positioned relative to the projector of the treatment device.

The patient support can, for instance, be mounted on a track or an telescopic arm to move the patient into and out of the treatment space. This allows for the patient to be fully prepared in a preparation room, be strapped to the patient support and then transported to the treatment room where the patient is positioned correctly relative to the projector.

This has as a particular advantage that the patient can be prepared outside of the patient treatment space and moved into the treatment space for irradiation. This reduces the time the patient has to spend in the treatment space. It also makes the procedure more efficient as possibly a second patient can be prepared on a separate patient support outside of the treatment space while a first patient is irradiated. Said second patient may than be moved to the treatment room when the first patient is done being irradiated.

In embodiments, the patient support is an extendable table, the table comprising:
  a table top for supporting a patient;
  a base, to for mounting the table to a support surface; and
  a movable arm configured to move the table top, with a patient supported thereon, relative to the base. The base is to be mounted outside the treatment space, and the moveable arm is configured to move the table top through the treatment space entry port into the treatment space and in alignment with the projector of the treatment device, and preferably to position the table top in the treatment space in at least two directions relative to the projector of the treatment device.

This has as a particular advantage that the patient can be prepared outside of the treatment space and be moved on the extendable table to the treatment space. The extendable table can be positioned precisely with respect to the radiation projector.

The table may be a comfortable table. The movable arm may move smoothly to give minimal discomfort to the patient while moving. The moveable arm may be able to adjust its position during irradiation to allow for irradiation of the proper part of the patient.

In an embodiment, the treatment space is dimensioned to hold the patient support table with a longitudinal axis perpendicular to the treatment axis, and allows for movement of the support table along its longitudinal axis while in this position to enable the patient to be moved by the table relative to the projector in a direction perpendicular to the treatment axis.

This allows the radiation device to irradiate a patient lying on the patient support table from more angles. It may be advantageous for treatment of the patient that the patient is placed perpendicular to the treatment axis.

In an embodiment, the patient support table comprises a control system, which control system is configured to adjust the position of the patient relative to the projector, which preferably is linked with a control system of the treatment device and/or is configured to link with a marker on the gantry and/or the treatment device to adjust the position of the support table relative to the projector of the treatment device.

This increases the precision of the irradiation process in the radiation assembly. The control system may precisely control how much radiation each part of the patient receives while being irradiated.

In an embodiment, the patient support table comprises a telescopic arm, configured for extending through the patient transfer opening and into the treatment space of the radiation device when the radiation device is in the docking position adjacent the preparation room, such that the patient can be moved into and moved out of the treatment space on the patient support table.

This is a particular simple and stable set up for moving the patient into and out of the treatment room.

The invention also relates to a radiation facility, which comprises:
- a radiation assembly according to the invention;
- multiple patient preparation rooms, each for preparing a patient for treatment, preferably for positioning a patient in a treatment positon on a patient support, which preparation rooms are each provided with a patient transfer port; and
- a gantry manipulator, configured to positon the gantry in a treatment position relative to each of the multiple patient preparation rooms, in which treatment position, the treatment space entry port of the gantry is aligned with the patient transfer opening of one of the patient preparation rooms, to enable direct transfer of a patient from the one of the preparation rooms into the treatment space.

The radiation facility with multiple preparation rooms may be used to prepare several patients while irradiating another patient thus increasing the efficiency of use of the radiation facility. The patients may be prepared and placed on the patient support in separate treatment rooms, said patient support then which moves the patients into position for treatment when each patient is ready and when the treatment room is in position for the respective patient.

The multiple preparation rooms do not need gantries since the radiation facility is provided with a gantry manipulator which is configures to position the gantry in a treatment position relative to a preparation room which houses a patient ready to be treated. When a patient is done being treated and moved out of the gantry the gantry manipulator may position the gantry to a new treatment position relative to another preparation room where a second patient was prepared while the first patient was being irradiated.

The gantry manipulator can for instance comprise tracks to move the gantry from one treatment position to the next.

In embodiments, the preparation rooms are provided with docking stations for securing the gantry relative to the preparation room in a predetermined position. The gantry manipulator may move the gantry relative to the preparation rooms. In order to prevent the gantry from moving relative to the preparation rooms the preparation rooms may be provided with docking stations to prevent such movement. This ensures that the gantry stays in its place and may prevent accidents.

In embodiments the gantry manipulator comprises hydraulic cylinders for lifting the gantry relative to multiple stacked preparation rooms.

The multiple preparation rooms may be stacked vertically with respect to each other. In order to lift the gantry between the different preparation rooms the gantry manipulator may be provided with hydraulic cylinders to lift the gantry. It may be advantageous to stack the preparation rooms between different floors of the radiation facility depending on the lay out of the radiation facility.

Another possible use of the hydraulic cylinders is to align the gantry with the treatment space entry port in a vertical direction. For example, aligning the gantry from a position for moving that is slightly lower than the treatment space entry port to a position aligned with the treatment space entry port.

In embodiments, the gantry manipulator comprises:
- a gantry track, the gantry track extending along the multiple preparation rooms,
- a gantry carriage for transporting the gantry over the transport track along the multiple preparation rooms, and
- a drive for moving the gantry carriage along the gantry track.

The gantry carriage has a carriage body that extends along a longitudinal axis, which longitudinal axis extends between a first end and an opposite second end, and wherein the patient treatment axis extends parallel to the longitudinal axis of the support carriage, and wherein the carriage is at each end guided by the gantry track.

In embodiments, the gantry, preferably a treatment housing of the gantry, forms the carriage body, preferably such that the first bearing and the second bearing are connected to a guiderail of the track, for example via a bogy are supported on a guide rail of the track, and the first bearing and the second bearing are connected to each other by a rotatable supported part of the gantry, preferably the treatment housing, only.

These embodiments are advantageous since they are compact and do not require a separate structure for the carriage body. The carriage body is formed from the gantry which is connected to a guiderail of the track through the first and second bearings.

The gantry and the gantry carriage can be relatively light and compact since the carriage is formed by the gantry. This is advantageous for transport of the gantry along the gantry track.

A compact structure is beneficial when mounting the gantry inside a building, for example inside a treatment facility.

In embodiments, the first end and the opposite second end of the cylindrical treatment space are located at the first end and the second end of the carriage respectively. This is advantageous since it simplifies the design of the radiation assembly.

In embodiments, the treatment device, when rotated in a position below the patient treatment axis, extends below the gantry track. This is advantageous since this allows for a weight distribution that is advantageous while transporting the gantry, namely it allows for a lower centre of mass, making the structure more stable.

In embodiments, the gantry track is a transport track, preferably a horizontal transport track, the transport track extending along the multiple preparation rooms, wherein the multiple preparation rooms are stacked next to each other preferably with their patient transfer ports in horizontal alignment, along the transport track, wherein the gantry carriage is supported by the transport track, for moving the gantry in a horizontal direction along the transport track and the multiple preparation rooms.

This is advantageous when the preparation rooms are located on the same floor. Allowing the gantry to be transported between the horizontally separated preparation rooms has all the advantages noted previously with regards to the multiple preparation rooms as well as it avoids having to lift the heavy gantry in a vertical direction.

In embodiments, the transport track comprises two guide rails, and the gantry carriage is at each end supported by one of the two guide rails. Hence the gantry is supported on both sides by the guide rails allowing for smooth horizontal movement and good support during transport.

In a further embodiment, the inner circular track is provided in the form of a bearing. This is beneficial in that it allows for providing the carriage with a stable support in combination with a track having a comparatively small radius.

In an embodiment, track comprises an inner circular track and an outer circular track, and the carriage comprise, in addition to the gantry a central hub, which central hub is mounted on the inner circular track. Preferably the inner circular track is provided in the form of a bearing, the bearing supporting the hub. Thus, the hub rotates with the gantry about a centre of the circular transport track, when the gantry is moved between treatment positions.

Thus, in such an embodiment, the gantry track comprises an outer track and an inner track, the inner track being embodied as a bearing. The carriage comprises the gantry and the supporting hub. The gantry is supported at one end on the outer track via a bogy or similar, and is supported on the opposite end by the hub, the hub being supported on the inner track, i.e. the bearing.

In an embodiment, the inner track, or bearing, supporting the hub, is located at a lower level, while the outer track is located at a higher level. In such an embodiment, the hub preferably clears the height needed between the inner track, more in particular the floor supporting the inner track, and the gantry to enable the gantry, more in particular the treatment device of the gantry, to rotate about the treatment axis.

In embodiments, the gantry track is a circular transport track, the transport track extending along the multiple preparation rooms, wherein the multiple preparation rooms are set up around a centre of the circular transport track.

The multiple preparation rooms may be set up in a square if they are four preparation rooms. Distributing the preparation rooms in a circle allows the gantry carriage to move in a circle, so the gantry carriage can move in a single direction, always encountering a preparation room where a patient is ready. This is advantageous compared to a linear set up where the gantry carriage may have to move back to the first preparation room.

In embodiments, the transport track comprises two concentric circular guide rails, and the gantry carriage is at each end supported by one of the two guide rails. This allows the carriage to be transported around the centre of the circle of preparation rooms while it is supported by two circular guide rails. Giving good support and stable transport.

In embodiments, the cylindrical treatment space has an entry port on each end, and on opposite sides of the gantry track are provided preparation rooms, and wherein the gantry track and the gantry carriage are dimensioned such that the when the carriage supports the treatment space with one end in a treatment position relative to a first patient treatment room, the opposite end of the treatment space is supported in a treatment position relative to a second patient treatment room This is advantageous since this allows the preparation of a first patient, in a circular set up, while a second patient is being irradiated. When the second patient is done being irradiated the first patient may be treated without moving the treatment space, increasing efficiency of use.

In embodiments the multiple preparation rooms are set up with the patient transfer port facing a centre of the circular treatment track, wherein the transport track comprises a circular circumferential guide rail, and the gantry carriage is at each end supported by the circumferential guide rail.

Advantageously the gantry carriage is positioned above the centre of the circular guide rail and rotates around the centre of the rail, creating a compact setup. Both end points of the carriage may be supported by the same guide rail.

In embodiments, the treatment space has an entry port on each end, and wherein the gantry track and the gantry carriage are dimensioned such that the when the carriage supports the treatment space with one end in a treatment position relative to a first patient treatment room, the opposite end of the treatment space is supported in a treatment position relative to a second patient treatment room.

This is another embodiment that advantageously allows for a first patient to be prepared while a second patient is being irradiated. Switching between patients can be done without moving the carriage.

In embodiments, the gantry track is a lift track, preferably a vertical lift track, the lift track extending along the multiple preparation rooms, wherein the multiple preparation rooms are stacked upon each other preferably with their patient transfer ports in vertical alignment, along the lift track, wherein the gantry carriage is guided by the lift track, for moving the gantry in a vertical direction along the lift track and the multiple preparation rooms, and wherein the lift track comprises four guide rails, and the gantry carriage is at each end coupled with two guide rails, one on each side of the treatment axis.

This allows a stable vertical set up with a gantry track. The gantry carriage is supported by four guide rails that support the gantry equally from four sides. Vertical movement of the gantry may be advantageous when the radiation facility comprises a multi-storied building with a relatively small base. Patients may be prepared in preparation rooms that are located on different floors of the radiation facility.

In embodiments, the manipulator comprises at least one gantry counterweight to balance the weight of the radiation assembly, the gantry preferably comprising a treatment device counterweight. This allows for a stable configuration with a low centre of mass during all stages of operation.

Advantageously, the treatment device counterweight and the gantry counterweight are the same counterweight.

In embodiments, the gantry track comprises a horizontal transport track and a vertical lift track, and wherein one track is moveably supported by the other track, and the gantry carriage is coupled with the moveable supported track, to enable movement of the gantry along an array of preparation rooms, i.e. multiple preparation rooms stack next to each other and stacked on top of each other.

This allows the combination of vertically and horizontally stacked preparation rooms. This allows for more ways to stack preparation rooms, for instance in an L-shape.

In embodiments the transport track supports a lift carriage, which lift carriage comprises a lift track, and wherein the gantry carriage is guided by the lift carriage, for moving the treatment device in a vertical direction preferably perpendicular to the transport track. This is a way to transport the treatment device in a vertical direction.

In embodiments, the gantry manipulator comprises two gantry counterweights to balance the weight of the radiation assembly, the gantry preferably comprising a treatment device counterweight, which gantry counterweights are provided at opposite ends of the track.

Providing the gantry manipulator with two counter weights gives a better weight distribution on the different tracks as well as a better centre of mass for the gantry manipulator In embodiments, the treatment space has an entry port on each end, and on opposite sides of the gantry track are provided preparation rooms, and wherein the gantry track and the gantry carriage are dimensioned such that the when the carriage supports the treatment space with one end in a treatment position relative to a first patient treatment room, the opposite end of the treatment space is supported in a treatment position relative to a second patient treatment room.

This allows the treatment room to be transported vertically and horizontally to two different preparation rooms where patients may be prepared. The patients may then be treated sequentially without transporting the treatment room either vertically or horizontally.

In embodiments. the gantry manipulator further comprises a gantry housing, the gantry housing enclosing the gantry, and being configured to move with the gantry, to contain radiation emitted by the treatment device Depending on the accelerator used it may be advantageous to provide the gantry manipulator with a gantry housing to protect the patient and staff from radiation emitted by the treatment device.

In embodiments of the radiation assembly the gantry manipulator is provided with a gantry storage, which gantry storage is configured to shield the surroundings from radiation emitted by the radiation device, and wherein the gantry manipulator is configured to position the radiation assembly, i.e. the radiation device gantry and the radiation device, in a storage position in the gantry storage.

For example, when the radiation facility is not being used, for example at night, the radiation assembly may be located in the gantry storage reducing risk of radiation leaking from the radiation facility by shielding the surrounding from radiation emitted by the radiation device. This may make the radiation facility safer.

The gantry storage may be a concrete bunker or a lead box designed to contain the radiation. The gantry storage may be made of any suitable material. For example, if the gantry storage is a lead box than the lead box has walls thick enough to shield surroundings from radiation emitted by the radiation device.

In embodiments of the radiation assembly the gantry storage has an entry and exit opening on one side, and the gantry manipulator is provided with a door for said opening, which door preferably is attached to the radiation assembly, such that the door can be moved in unison with the radiation assembly by the gantry manipulator, and such that when the radiation assembly is moved into the storage position, the door is moved in a closing position in which it seals the entry and exit opening of the gantry storage.

For example, when the gantry storage is a concrete bunker, the gantry can be moved into the bunker through an entry opening of the bunker. The gantry housing then comprises a bunker door that closes and seals the bunker when the gantry is in the storage position. thus, there is no need for a hinged door, which allows for a compact configuration of the gantry storage.

In an alternative embodiment, the door is connected with the storage, e.g. is a hingable supported door, or is a sliding door. In such an embodiment, the door does not move with the radiation assembly, when the latter is moved along the rooms.

The invention further provides a radiation facility in which the radiation assembly is in a fixed position, and wherein multiple preparation rooms are provided that can be moved relative to the radiation assembly.

In an embodiment, the invention further relates to a radiation facility, the radiation facility comprising:

a radiation assembly according to one or more of the claims 1-13;

multiple patient preparation rooms, each for preparing a patient for treatment, preferably for positioning a patient in a treatment positon on a patient support, which preparation rooms are each provided with a patient transfer port; and a patient preparation room manipulator, configured to positon the multiple patient preparation rooms in a treatment position, in which treatment position, the treatment space entry port of the gantry is aligned with the patient transfer opening of one of the patient preparation rooms, to enable direct transfer of a patient from one of the preparation rooms into the treatment space.

The radiation facility with multiple preparation rooms may be used to irradiate a single patient while preparing one or more other patients thus increasing the efficiency of use of the radiation facility. The patients may be prepared and placed on the patient support in separate treatment rooms, said patient support than moves the patients into position for treatment when the respective patient is ready and when the treatment room is in position for the respective patient.

In an embodiment, the radiation facility is provided with a patient preparation room manipulator which is configures to position the multiple patient preparation rooms in a treatment position relative to the gantry. When a patient treated ends, and the patient is moved out of the radiation assembly, the patient preparation room manipulator may position the patient preparation rooms to a new treatment position wherein the radiation assembly can receive a second patient from a second preparation room, in which the second patient was prepared while the first patient was being irradiated.

In embodiments of the radiation facility the preparation rooms are provided with docking stations for securing the gantry relative to the preparation room in a predetermined position, preferably in which predetermined position, a preparation room is in the treatment position.

The patient preparation room manipulator may move the patient preparation rooms relative to the gantry. In order to prevent the preparation rooms from moving relative to the gantry the preparation rooms may be provided with docking stations to prevent such movement.

This ensures that the patient preparation room stays in its place and may prevent accidents.

In embodiments of the radiation facility the patient preparation room manipulator comprises:
- a patient preparation room track, the patient preparation room track extending along the gantry,
- a patient preparation room carriage for transporting the multiple patient preparation rooms over the transport track along the gantry, and
- a drive for moving the patient preparation room carriage along the patient preparation room track;
- wherein the multiple patient preparation rooms are transported over the transport track along the gantry for allowing the multiple patient preparation rooms to be placed in the treatment position.

In embodiments of the radiation facility the patient preparation room track is a transport track, preferably a horizontal transport track, the transport track extending along the gantry, wherein the multiple preparation rooms are stacked next to each other preferably with their patient transfer ports in horizontal alignment, along the transport track, and wherein the patient preparation room carriage is supported by the transport track, for moving the patient preparation rooms in a horizontal direction along the transport track and the gantry.

The patient preparation rooms may advantageously be supported by the transport track.

In embodiments of the radiation facility the transport track comprises two guide rails, and the patient preparation room carriage comprises two sides and is at each side supported by one of the two guide rails. This allows for a compact setup of the transport track.

The invention further provides a radiation facility in which the radiation assembly is in a fixed position, wherein the radiation assembly is provided with entry ports on both sides of the treatment space, wherein at each entry ports provided at least one preparation room, and at least at one of the two entry ports multiple preparation rooms are provided. In a further preferred embodiment, the multiple moveable preparation rooms are provided at each of the entry ports.

According to the invention, the patients are preferably entered into the treatment space from a preparation room on a preparation table, which patient table preferably is an extendable table, comprises a base mounted in the preparation room and a movable arm that can extend from the preparation room into the treatment space.

It is noted that while the patient is supported by such a table in the treatment space, the preparation room can not be moved relative to the treatment space. Thus, only after the patient has been treated, and has been brought back into the preparation room, a new preparation room can be moved into a treatment position. In such an embodiment, i.e. with a treatment space with a single entry, the preparation rooms can only be moved in between subsequent treatments.

It is submitted that the radiation assembly according to the invention enables to provide the treatment space with entry ports on opposite sides, and thus allows for entering patients into the treatment space from opposite sides. Thus, while the treatment rooms at one entry port can temporarily not be moved due to a patient being treated, the treatment rooms at the opposite entry port can be moved. Therefore, at that side the duration of the treatment is available to change preparation rooms, which in turn allows for slow movement of the rooms, reducing a possible negative influence of the movement on the patient in the preparation room. Furthermore, this allows for a minimum delay between subsequent treatments.

Therefore, in a preferred embodiment of the radiation facility, the cylindrical treatment space has an entry port on each end, and multiple patient preparation rooms are provided on both ends of the cylindrical treatment space,
- wherein the patient preparation rooms comprises a first group of patient preparation rooms at a first of the both ends and a second group of patient preparation rooms at a second of the both ends,
- wherein the preparation rooms of the first group are supported by a first patient preparation room manipulator, preferably comprising a first transport track, and wherein the patient preparation rooms of the second group are supported by a second patient preparation room manipulator, preferably comprising a second transport track,
- wherein the first patient preparation room manipulator is configured to positon each of the patient preparation rooms of the first group in a treatment position, in which treatment position, the treatment space entry port of the gantry at the first end is aligned with the patient transfer opening of one of the patient preparation rooms of the first group, to enable direct transfer of a patient from the preparation room into the treatment space; and
- wherein the second patient preparation room manipulator is configured to positon each of the patient preparation rooms of the second group in a treatment position, in which treatment position, the treatment space entry port of the gantry at the second end is aligned with the patient transfer opening of one of the patient preparation rooms of the second group, to enable direct transfer of a patient from the preparation room into the treatment space.

This embodiment is advantageous since it allows the preparation of a first patient in a patient preparation room of the first group while a second patient, which was prepared in a second patient preparation room of the second group, is being irradiated. When the treatment of the second patient is over, the first patient may be treated without moving the patient preparation rooms, increasing efficiency of use. Further patients may be prepared in further rooms which may be moved in position as another patient is being irradiated.

In an embodiment of the radiation facility the gantry manipulator further comprises a gantry housing enclosing the gantry and the radiation assembly to contain radiation emitted by the treatment device, the gantry housing having two openings that each allow access to one of the two entry ports of the treatment device. This may decrease leaking of radiation from the treatment device and increase security.

The invention further relates to a method for moving a gantry comprising a treatment device according to one or more of the claims 1-13 from a first treatment position adjacent a first preparation room to a second treatment position adjacent a second preparation room, using a gantry manipulator of a radiation facility according to one or more of the claims 14-34

In embodiments, the method further comprises: moving the gantry from a first treatment position adjacent a first preparation room to a second treatment position adjacent a second preparation room.

In embodiments, the method further comprises: positioning the treatment device below the treatment axis, preferably below a patient support table located in the treatment space.

In embodiments, the method further comprises:
entering a patient into the treatment space via the treatment space entry port;
positioning the patient in the treatment space relative to the projector of the treatment device;
rotating the treatment device about the treatment axis over an angle, preferably over an angle of at least 180 degrees, for example over an angle of more than 360 degrees.

In embodiments. the method further comprises:
positioning a patient on a treatment table prior to entering the patient into the treatment space;
entering the patient into the treatment space on the treatment table via the treatment space entry port.

The invention further relates to a method for moving the patient support table from one of the preparation rooms into the treatment space of the gantry of the radiation facility according to one or more of the claims 37-41, the method comprising;
moving the preparation room in the treatment position wherein the preparation room is adjacent to the gantry using the gantry manipulator, and
moving the patient support table via the treatment space entry port into the treatment space.

In embodiments of the method for moving the patient support table from one of the preparation rooms of the first group into the treatment space of the gantry of the radiation facility the method further comprises;
use the first patient preparation manipulator to move the preparation room of the first group into the treatment position at the first end of the gantry, in which treatment position the preparation room is adjacent to the gantry,
moving the patient support table from a first preparation room of the second group of preparation rooms, which first preparation room is located in the treatment position at the second end of the gantry, out of the treatment space via the treatment space entry port at the second end of the gantry,
moving the patient support table of the preparation room of the first group into the treatment space via the treatment space entry port at the first end of the gantry;
using the second patient preparation manipulator to move the first preparation room out of the treatment position and to simultaneously move a second preparation room of the second group into the treatment position at the second end of the gantry.

In embodiments the method further comprises: positioning the treatment device below the treatment axis, preferably below a patient support table located in the treatment space.

In embodiments the method further comprises:
positioning the patient support table in the treatment space relative to the projector of the treatment device;
rotating the treatment device about the treatment axis over an angle, preferably over an angle of at least 180 degrees, for example over an angle of more than 360 degrees.

In embodiments the method further comprises:
positioning a patient on the patient support table to be moved into the treatment space, prior to entering the patient support table into the treatment space, preferably prior to moving the respective preparation room into the treatment position;
entering the patient into the treatment space on the patient support via the treatment space entry port.

Advantageous embodiments of the radiation assembly according to the invention and the method according to the invention are disclosed in the sub claims and in the description, in which the invention is further illustrated and elucidated on the basis of a number of exemplary embodiments, of which some are shown in the schematic drawing. In the figures, components corresponding in terms or construction and/or function are provided with the same reference numbers.

DETAILED DESCRIPTION OF THE INVENTION

Whilst primarily presented for illustrative purposes with reference to one or more of the figures, any of the technical features addressed below may be combined with any of the independent claims of this application either alone or in any other technically possible combination with one or more other technical features.

Figure 1:
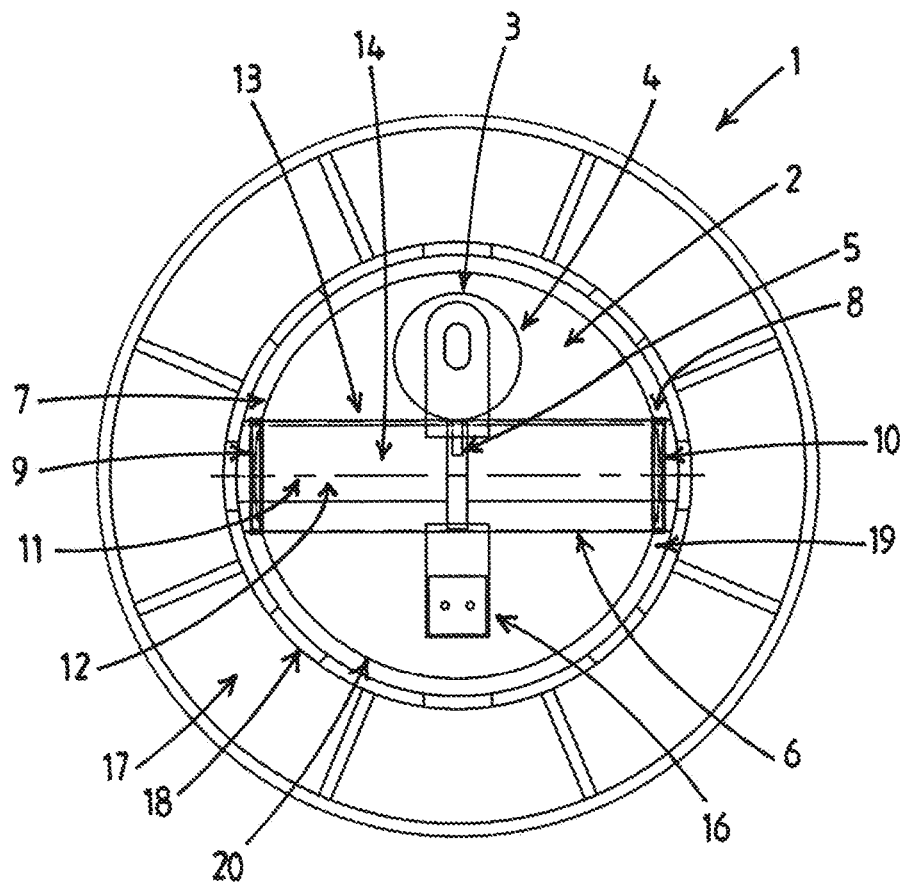
FIG. 01 shows a top view of a first exemplary embodiment of a radiation facility comprising a radiation assembly according to the invention.

FIG. 1 shows a top view of a first exemplary embodiment of a radiation facility (1) comprising a radiation assembly (2) according to the invention. The radiation assembly (2) comprises a radiation device (3), preferable a proton radiation treatment device, wherein the treatment device comprises an accelerator (4), and a radiation projector (5). The radiation assembly (2) further comprises a gantry (6) that moveable supports the accelerator (4) and the projector (5).

The gantry (6) provides a range of movements of the radiation device (3) that defines a cylindrical treatment space which has the patient treatment axis (12) at its centre. The cylindrical treatment space extends between a first end (7) end a second opposite end (8). The gantry comprises a first slew bearing (9) and a second slew bearing (10) to moveable support the treatment device (3), which slew bearings have a central rotational axis (11) that aligns with the patient treatment axis (12).

The first slew bearing has a central opening (not shown) that defines a treatment space entry port for moving a patient into and out of the treatment space.

The radiation assembly (2) further comprises a cylindrical shaped treatment housing (13) that fully encloses the treatment space (14). The treatment housing (13) is supported at opposite ends by the first slew bearing (9) and the second slew bearing (10).

The gantry (6) further comprises a treatment device counterweight (16) used to balance the weight of the radiation device (3).

The radiation facility (1) comprises multiple patient preparation rooms (17) designed for preparing patients for treatment. Each patient preparation room (17) is provided with a patient transfer port (18). The preparation rooms (17) in the embodiment of FIG. 1 are aligned horizontally.

The radiation facility (1) further comprises a gantry manipulator (19) for positioning the gantry in a treatment position relative to each of the multiple preparation rooms (17). The gantry manipulator comprises a gantry track (20), for instance rails, for transporting the gantry (6) along the multiple preparation rooms (17).

In FIG. 1 the gantry carriage (21) is formed from the treatment housing (13).

The gantry track (20) of FIG. 1 is a circular transport track (20), that extends along the multiple preparation rooms (17) which are placed in a circular set up. The gantry carriage (21) is supported on both sides by the same gantry track (20).

The multiple preparation rooms (17) are set up with the patient entry port (18) facing a centre of the circular gantry track (20) and the gantry carriage (21) rotates around the centre of the circular gantry track (20).

The gantry track (20), the gantry carriage (21), and the treatment space (14) are dimensioned such that the when the carriage (21) is aligned with a first preparation room (17) on the first end (7), than the carriage (21) is also aligned with a second preparation room (17) on the second end (8).

The treatment space (10) can be accessed both from the first end (7) and the second end (8) through respectively the first slew bearing (9) and the second slew bearing (10), in this embodiment patients may enter from distinct preparation rooms (17), without moving the gantry (6) in between treatments.

Figure 2:
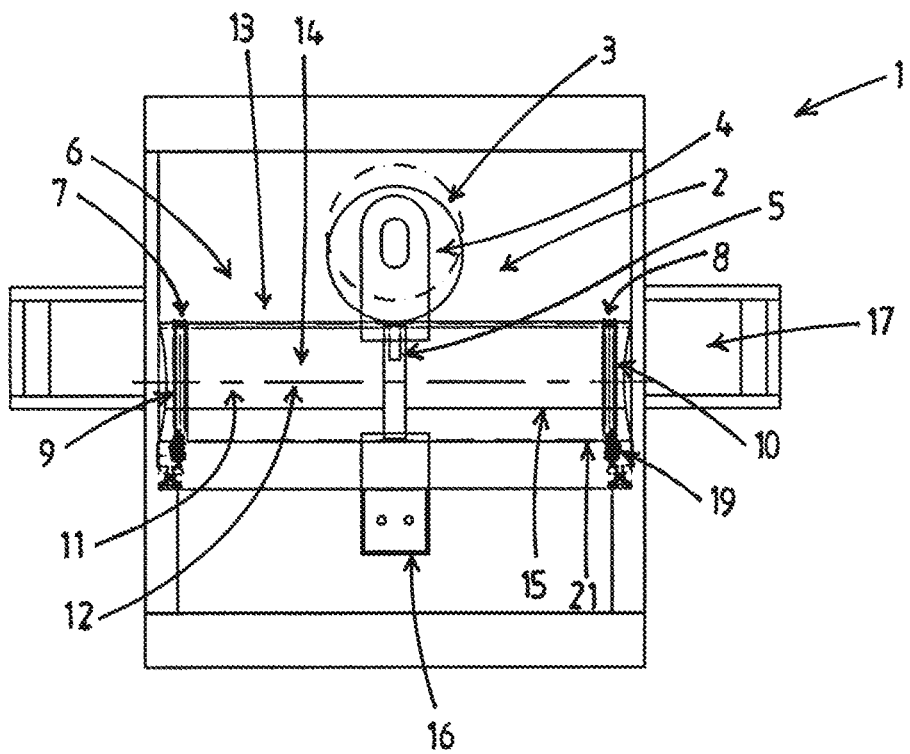
FIG. 02 shows a side view in cross section of the radiation facility of FIG. 1.

FIG. 2 shows in side view a cross section of the radiation facility (1) of FIG. 1. In side view a treatment floor (15) is visible, which is located inside the treatment housing (13). The treatment floor (15) may be used to support additional equipment of allow a person to walk into the radiation assembly (2).

As shown in FIG. 2 by the dashed lines around the treatment device (3), the treatment device (3) may be moved in a direction perpendicular to the patient treatment axis (12). This allows the projector (5) to be moved upwards as a patient enters the treatment space (14) and may also be used during treatment to improve the treatment effectiveness.

Figure 3:
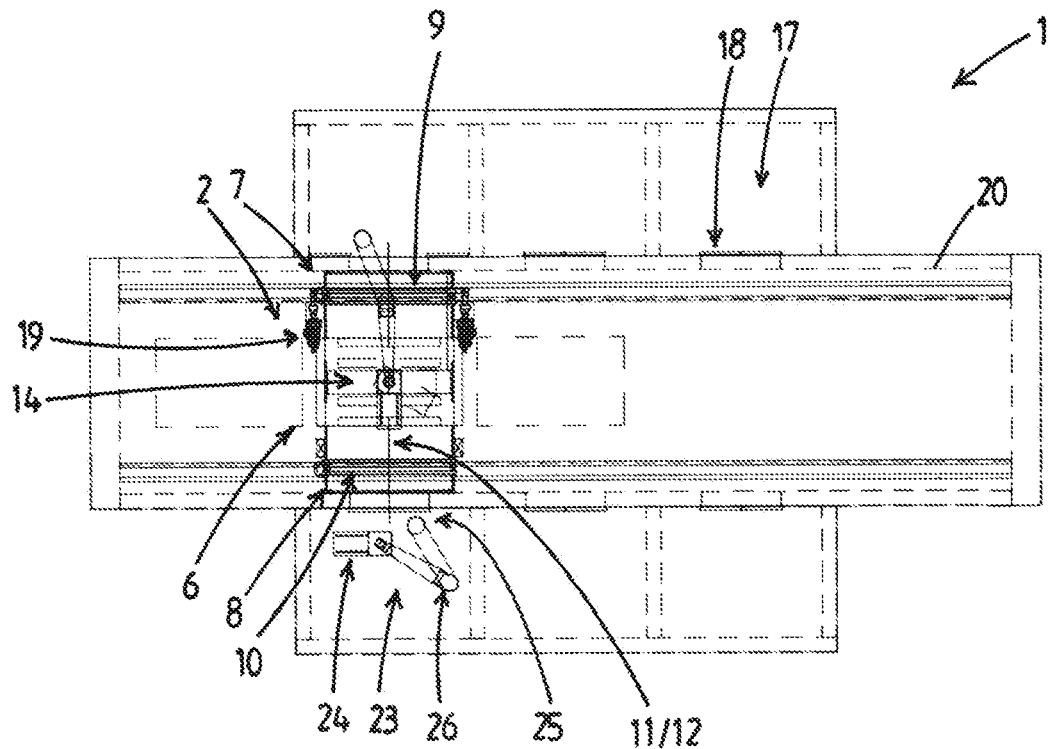
FIG. 03 shows a top view of a second exemplary embodiment of a radiation facility comprising a radiation assembly according to the invention.
Figure 4:
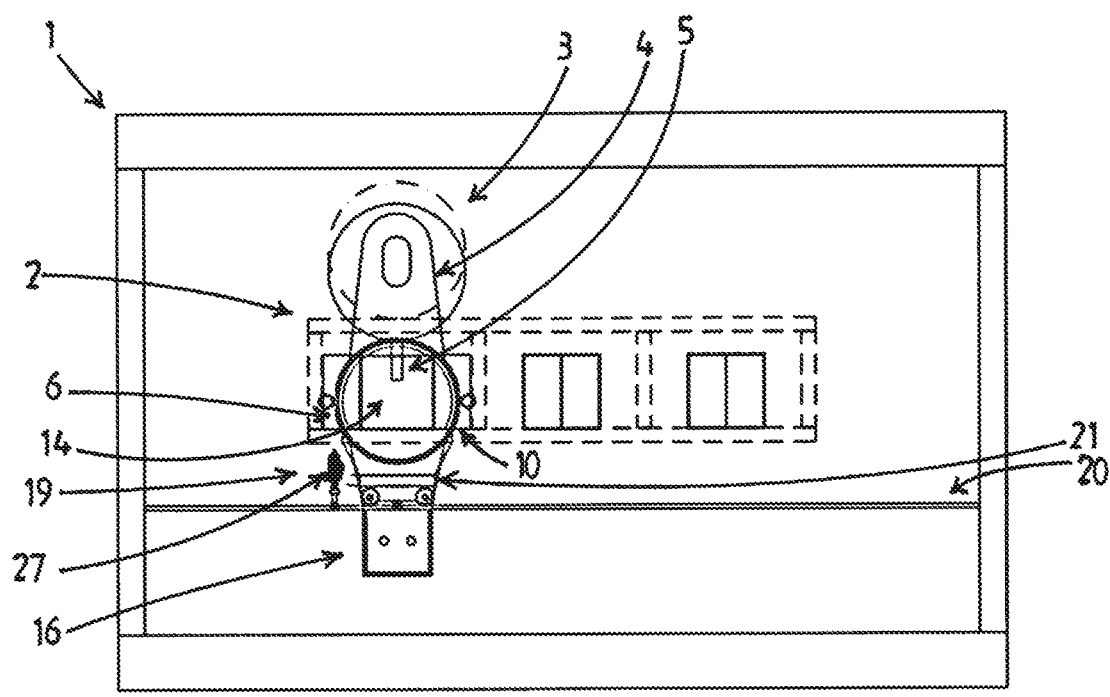
FIG. 04 shows a side view in cross section of the radiation facility of FIG. 3.

FIG. 3 and FIG. 4 show a second exemplary embodiment of a radiation facility (1) according to the invention.

FIG. 3 shows a top view of the second exemplary embodiment of a radiation facility (1) comprising a radiation assembly (2) according to the invention and FIG. 4 shows a side view in cross section of the radiation facility of FIG. 3. The radiation assembly (2) comprises a radiation device (3), preferable a proton radiation treatment device, wherein the treatment device comprises an accelerator (4), and a radiation projector (5). The radiation assembly (2) further comprises a gantry (6) that moveable supports the accelerator (4) and the projector (5).

The gantry carriage (21) is supported on linear gantry tracks (20) that extend horizontally along multiple patient preparation rooms (17). The carriage is driven by a carriage drive (27).

The treatment space (14) has a patient entry port (18) on both sides and the gantry track (20) and the gantry carriage (21) are dimensioned such that when the carriage (21) supports the treatment space (14) with the first end (7) in a treatment position relative to a first preparation room (17), the second end (8) of the treatment space (14) is supported in a treatment position relative to a second preparation room (17).

The radiation assembly (1) of FIGS. 3 and 4 is equipped with a number of patient supports (23). The patient supports (23) are mounted in the preparation rooms (17) on a base (25).

The patient may be supported on a table top (24) which is connected to the base (25) by a moveable arm (26). The moveable arm (26) is configured to move the table top (24) with the patient supported thereon relative to the base (25).

The moveable arm (26) is configured to move the table top (24) with the patient through the patient entry port (18) into the treatment space (14). The table top (24) may be positioned inside the treatment space (14) in at least two direction relative to the projector (5) to allow the correct area of the patient to be irradiated.

The table top (24) may be rotatable on the moveable arm (26) relative to the patient treatment axis (12) inside the patient treatment space (14).

Figure 5:
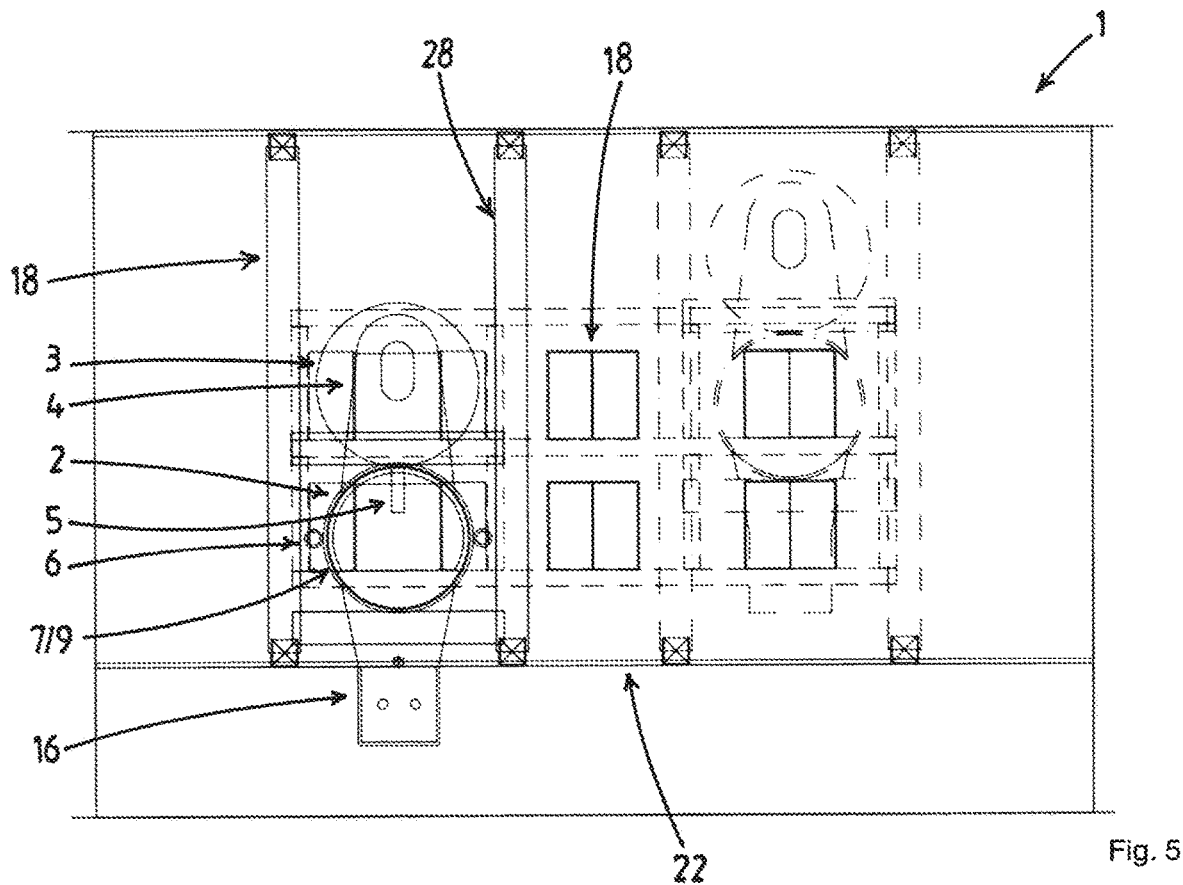
FIG. 05 shows a side view in cross section of a third exemplary embodiment of a radiation facility comprising a radiation assembly according to the invention.

FIG. 5 shows a side view of a third exemplary embodiment of a radiation facility (1) comprising a radiation assembly (2) according to the invention. The radiation assembly (2) is drawn in two exemplary positions in the radiation facility (1).

The gantry track (20) has a vertical lift component (28) and a horizontal transport component. The lift track (28) extends along multiple vertically stacked preparation rooms (17). The preparation rooms are stacked with their patient entry ports (18) in vertical alignment.

The gantry carriage (21) is guided by the lift track (28) for moving the gantry in a vertical direction.

The horizontal component of the gantry track (20) is the transport track (22). The horizontal track (22) and the lift track (28) may be moveable supported by the respective other track.

The gantry carriage (21) is enabled to move in both vertical and horizontal directions by the gantry track (20) to align with preparation rooms (17) that are stacked both vertically and horizontally.

Figure 6:
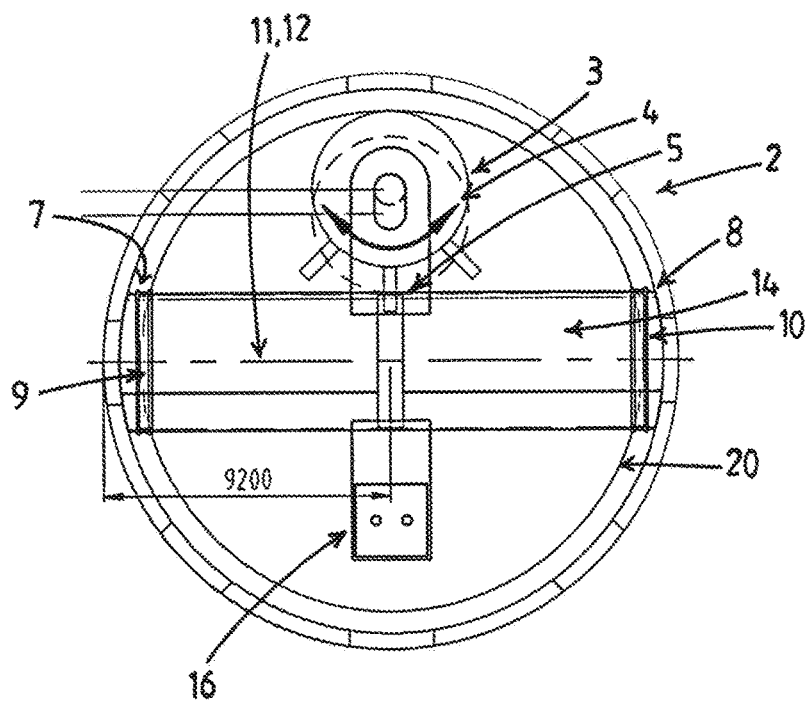
FIG. 06 shows a top view of a radiation assembly according to the invention.

FIG. 6 shows a top view of a radiation assembly (2) according to the invention with the radiation device (3) and the counter weight (16) tilted with respect to a vertical.

The radiation device (3) of FIG. 6 may be pivoted relative to an axis extending perpendicular to the patient treatment axis (12). Hereby the projector (5) is pivoted relative to a patient supported in the treatment space (14), allowing the patient to be irradiated from additional angles.

Figure 7:
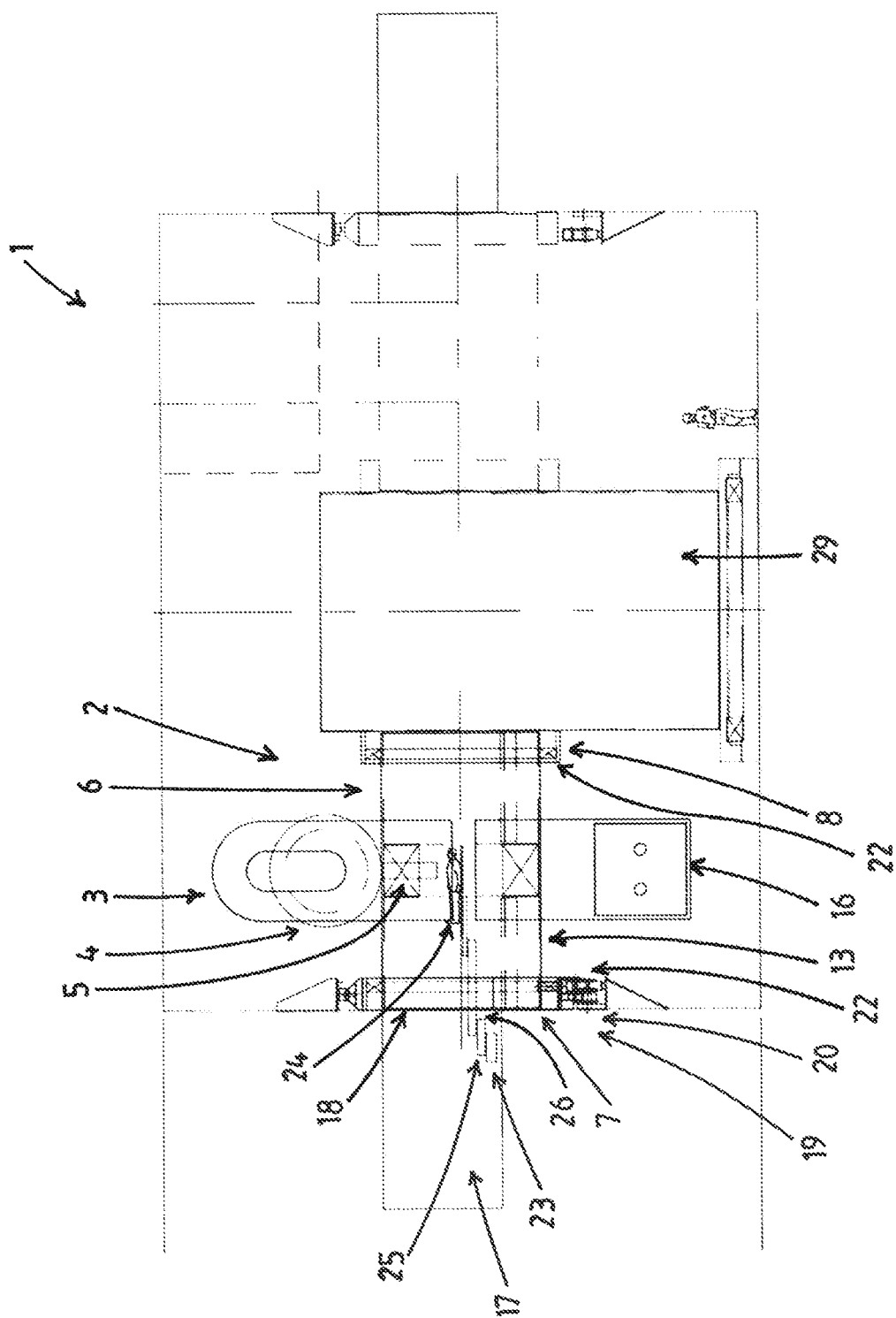
FIG. 07 shows a side view in cross section of a fourth exemplary embodiment of a radiation facility in a first position according to the invention.
Figure 8:
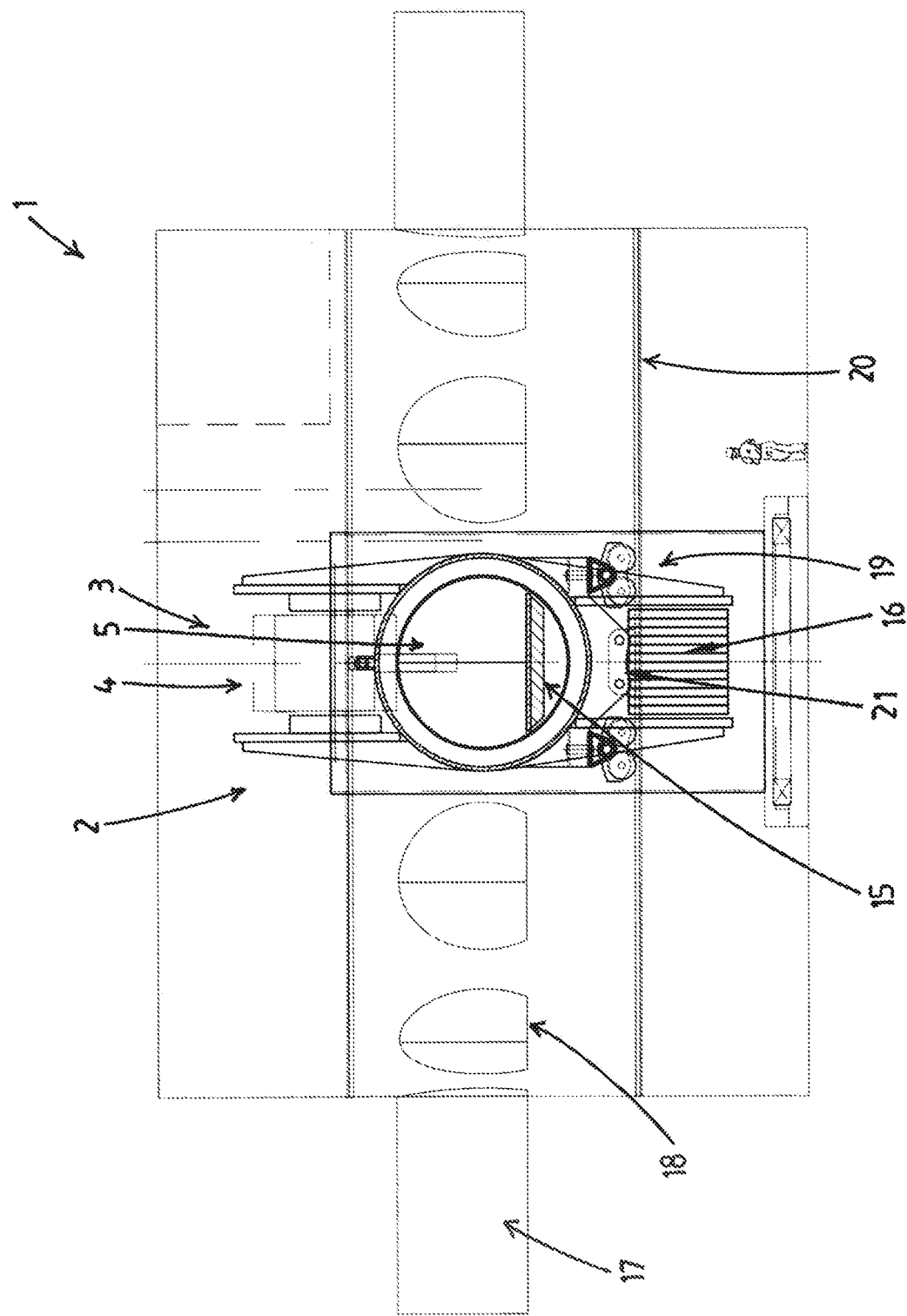
FIG. 08 shows a side view in cross section of the fourth exemplary embodiment of a radiation facility in a second position according to the invention.

FIGS. 7 and 8 show a fourth exemplary embodiment of a radiation assembly (2) according to the invention.

FIG. 7 shows a side view in cross section of a radiation facility (1) according to the invention in a first position and FIG. 8 shows a side view in cross section of the radiation facility (1) in a second position.

The radiation assembly (2) comprises a radiation device (3), preferable a proton radiation treatment device, wherein the treatment device comprises an accelerator (4), and a radiation projector (5). The radiation assembly (2) further comprises a gantry (6) that moveable supports the accelerator (4) and the projector (5).

The gantry (6) is transported by a gantry carriage (21) which is supported by a gantry track (20) comprising a first transport track (22) and a second transport track (22) that run in two concentric circles. The first transport rack (22) runs along preparation rooms (17) in which patients may be prepared for treatment and the second transport track runs along a central hub (29) which is located in the centre of the radiation facility (1).

The central hub (29) supports gantry carriage (21) and may also provide the radiation device (3) with resources such as electricity for powering the accelerator (4).

FIG. 7 shows the radiation assembly (2) in a first position where a patient is supported by a table top (24) in a treatment space (14). The table top (24) is connected to a base (25) by a moveable arm (26). The patient may be irradiated by the radiation device (3) FIG. 8 shows the radiation assembly (1) in a second position where the patient is removed from the treatment space (14) and the radiation assembly is rotated by 90 degrees and may be aligned with another patient preparation room (17), for example to receive a second patient from said patient preparation room (17).

Figure 9:
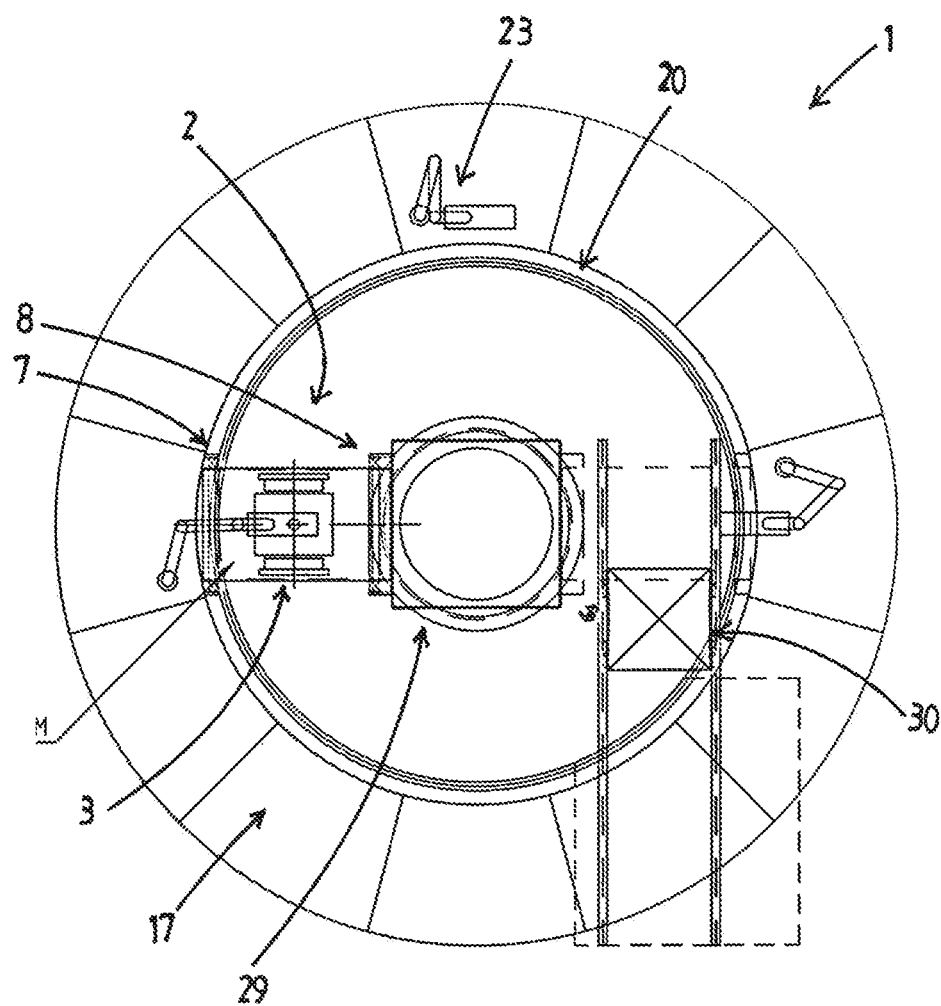
FIG. 09 shows a top view of a radiation facility according to the invention.

FIG. 9 shows a top view of a radiation facility (1) according to the invention where the radiation assembly (2) is supported by gantry tracks (20) that are concentric. The second end (8) of the radiation assembly (2) is supported by a central hub (29) which is supported by the inner gantry track (20). In this embodiment, the central hub (29) rotates with the radiation assembly (2) as it moves between preparation rooms (17).

Multiple preparation rooms (17) are equipped with patient supports (23) for moving patients from the preparation rooms (17) into the treatment space (14).

The radiation facility (1) is further equipped with a trolley (30) for removing and installing parts of the radiation assembly (2) such as the radiation device (3). For example, said trolley (30) may be useful when parts of the radiation assembly (2) have to be removed for maintenance.

Figure 10:
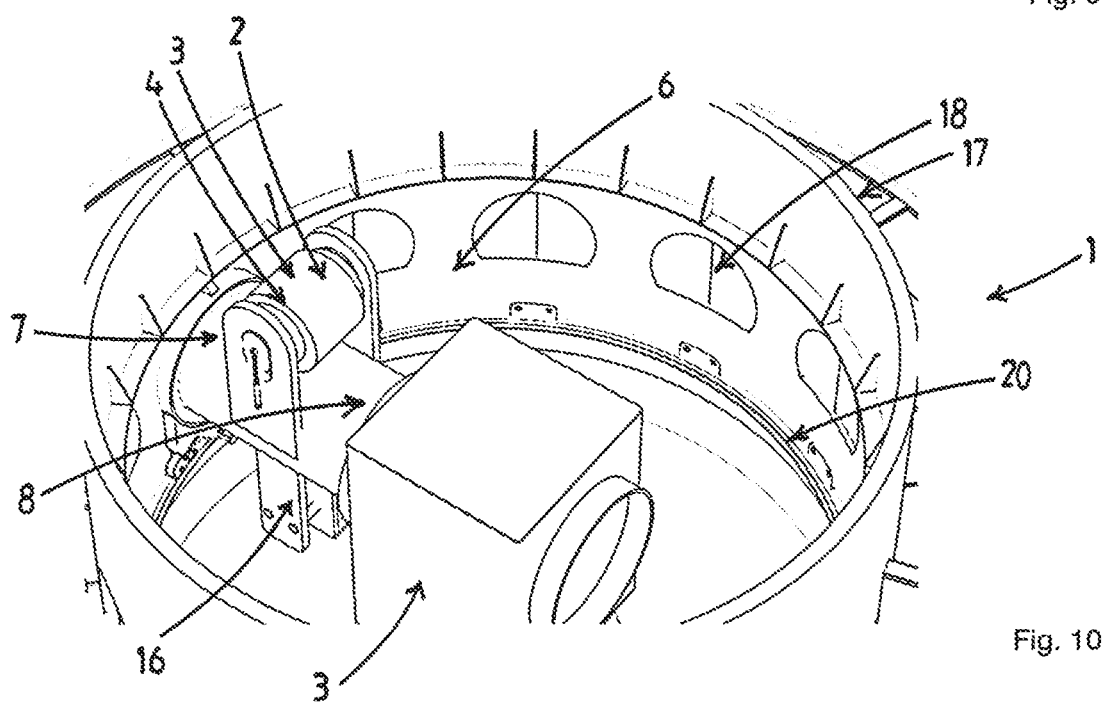
FIG. 10 shows a computer drawing of a radiation facility according to the invention.

FIG. 10 shows a computer drawing of a radiation facility (1) according to the invention. The radiation facility comprises a radiation assembly (2), which comprises a radiation device (3), preferable a proton radiation treatment device, wherein the treatment device comprises an accelerator (4) and a counterweight (16). The radiation assembly (2) further comprises a gantry (6) that moveable supports the accelerator (4). The radiation assembly is supported by gantry tracks (20) which are located in concentric circles. The outer gantry track (20) runs along multiple patient preparation rooms (17) which may be accessed by patient entry ports (18) and the inner gantry track (20) supports a central hub (29) which supports the gantry (6) on its second end (9).

Figure 11:
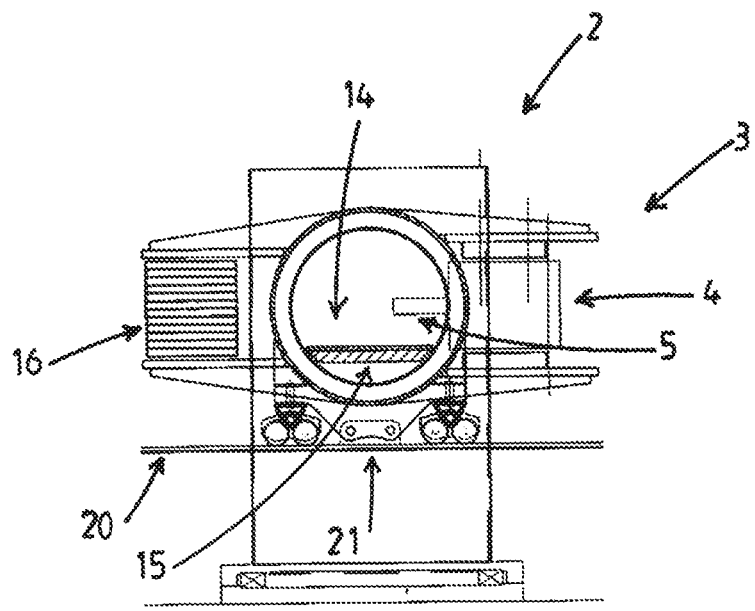
FIG. 11 shows a radiation assembly according to the invention.

FIG. 11 shows a radiation assembly (2) according to the invention, where the radiation device (3) and the counter weight (16) are rotated by 90 degrees relative to a vertical. In this figure the projector (5) points along a horizontal.

Figure 12:
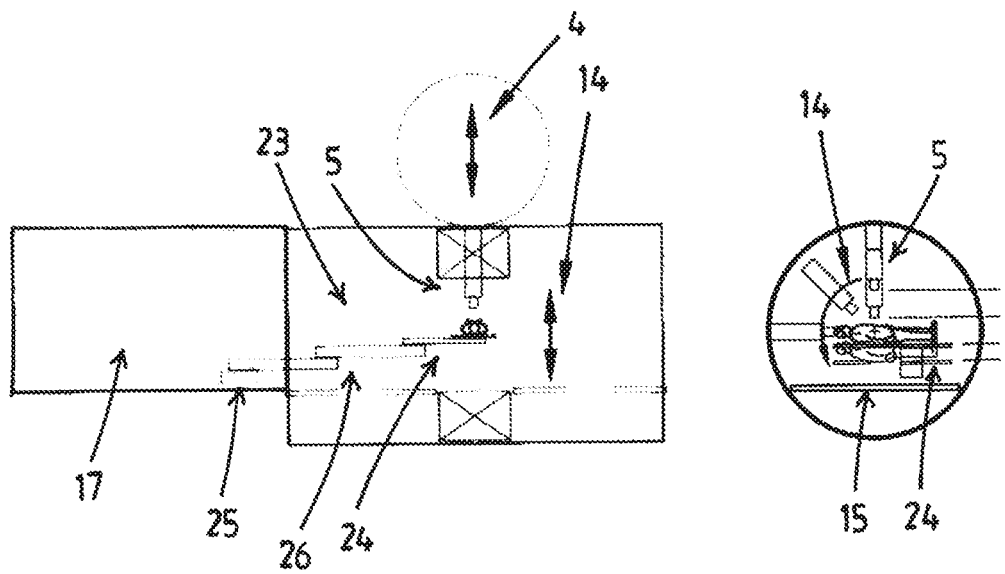
FIG. 12 shows a side view and an axial view of a patient treatment room according to the invention.

FIG. 12 shows a patient treatment room (14) according to the invention with a patient supported on a patient support (23). The radiation device (3) is vertically movable. Vertical movement of the radiation device (3) results in vertical movement of the projector (5). This changes de distance between the patient and the projector (5) and may influence the irradiating of the patient. Said patient is oriented perpendicular to the treatment axis (12).

Figure 13:
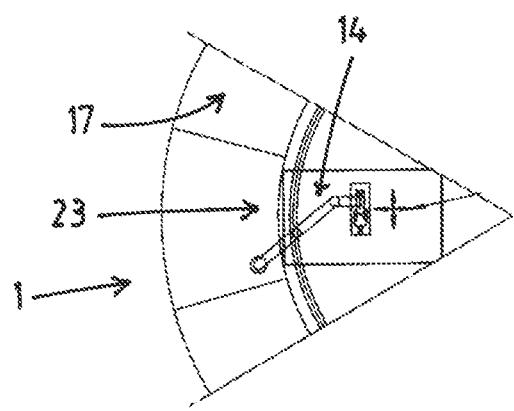
FIG. 13 shows a top view of the patient treatment room of FIG. 12.

FIG. 12 also shows a rotational movement of the projector (5) relative to a patient supported on a table top (24). The patient is oriented perpendicular to a treatment axis (12) and the projector (5) moves along a longitudinal direction relative to the patient. FIG. 13 shows a patient treatment room according to the invention where a patient is supported by a patient support (23). The patient is oriented perpendicular to the patient treatment axis (12). Possible horizontal movement of the patient is indicated in the figure.

Figure 14:
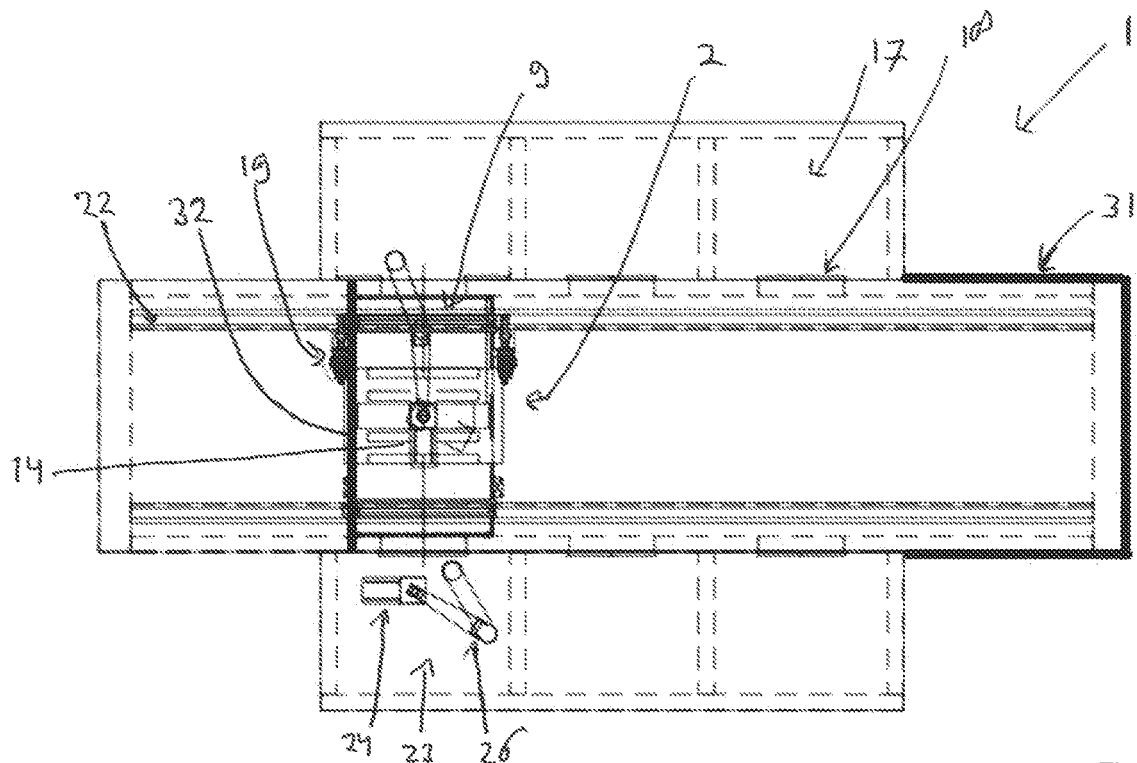
FIG. 14 shows a top view of a second exemplary embodiment of a radiation facility comprising a radiation assembly and a radiation storage according to the invention.

FIG. 14 shows a top view of a second exemplary embodiment of a radiation facility (1) comprising a radiation assembly (2) and a gantry storage (31) according to the invention.

The radiation assembly (2) comprising the gantry (6) may be moved into a storage position wherein the radiation assembly (2) is located inside the gantry storage (31). The gantry storage comprises side walls, a floor and a roof that enclose the radiation assembly (2) in the storage position on all but one side. The gantry storage (31) is sealed by the gantry storage door (32) which closes and seals the gantry storage (31) when the radiation assembly is in the storage position. Thus when the radiation assembly (2) is located in the storage position the radiation facility (2) is fully enclosed such that surroundings are protected from radiation emitted by the treatment device.

Figure 15:
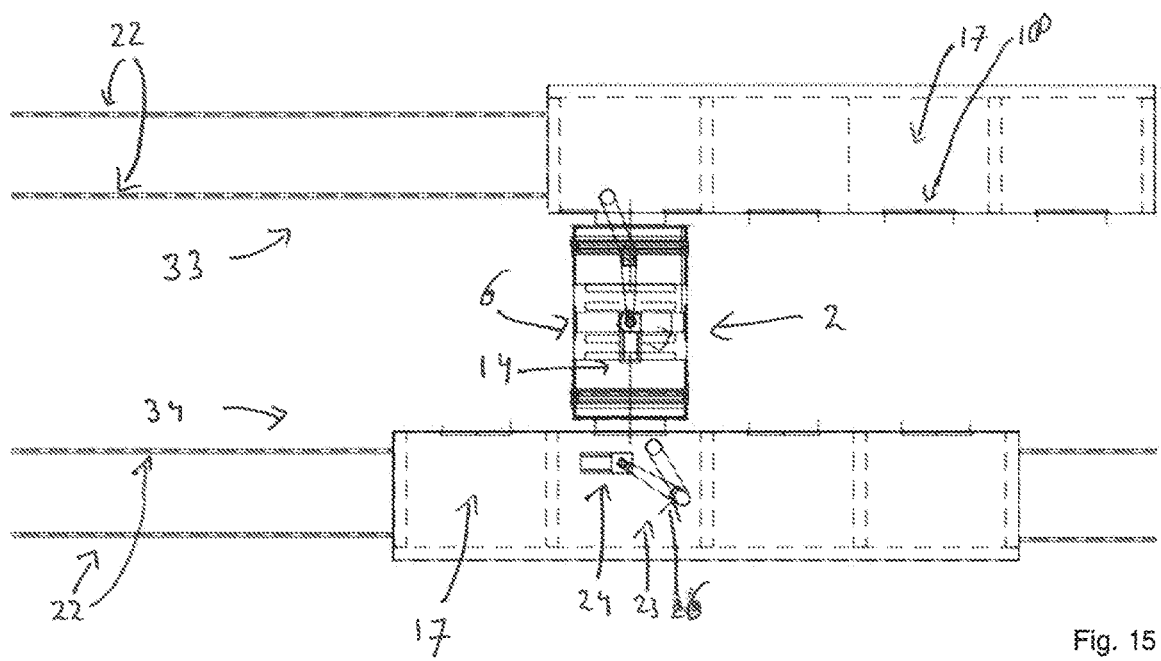
FIG. 15 shows a top view of a fifth exemplary embodiment of a radiation facility comprising a first and a second patient treatment room manipulator according to the invention.

FIG. 15 shows a top view of a fifth exemplary embodiment of a radiation facility (1) comprising a patient treatment room manipulator according to the invention. The radiation facility comprises a first group of patient preparation rooms (33) and a second group of patient preparation rooms (34). in the particular embodiment shown, the preparation rooms of the first group (33) and of the second group (34) are placed on tracks (22) which allow the preparation rooms (17) of the two groups to move independently from the preparation rooms of the other group.

The preparation rooms of the first group (33) may be moved independently from the preparation rooms of the second group (34) to respective treatment positions. In the figure the first treatment room from the left of the first group (33) and the second treatment room from the left of the second group (34) are in the treatment position such that patients in these rooms may enter the radiation assembly for treatment.

While a patient prepared in the first group (33) is irradiated a patient of the second group (34) may be prepared for irradiation. This setup allows near constant uptime of the radiation assembly (2) because several patients may be prepared while another patient is irradiated.

The patients may enter the radiation assembly after irradiating of a previous patient is finished with a minimum downtime of the radiation assembly. The setup also increases patient comfort since the patients may be transported from the patient preparation room (17) to the radiation assembly (2) by the patient support (23).

Other variations to the disclosed embodiments can be understood and effected by those skilled in the art in practicing the claimed invention, from study of the drawings, the disclosure, and the appended claims. In the claims, the word "comprising" does not excluded other elements or steps, and the indefinite article "a" or "an" does not exclude a plurality. A single processor or other unit may fulfil the functions of several items recited in the claims.

The mere fact that certain measures are recited in mutually different dependent claims does not indicate that a combination of these measured cannot be used to advantage. Any reference signs in the claims should not be construed as limiting the scope.

The invention is by no means limited to the exemplary embodiment described herein above, but comprises various modifications hereto, in so far as they fall within the scope of the following claims.

REFERENCE IS MADE TO THE FOLLOWING REFERENCE NUMBERS

1 Radiation facility
2 Radiation assembly
3 Radiation device
4 Accelerator
5 Projector
6 Gantry
7 First end
8 Second end
9 First slew bearing
10 Second slew bearing
11 Central rotational axis
12 Patient treatment axis
13 Treatment housing
14 Treatment space
15 Treatment floor
16 Counterweight
17 Preparation room
18 Patient entry port
19 Gantry manipulator
20 Gantry track
21 Gantry carriage
22 Transport track
23 Patient support
24 Table top
25 Base
26 Moveable arm
27 Drive
28 Lift track
29 Central hub
30 Trolley
31 Gantry storage
32 Gantry storage door
33 First group of patient preparation rooms
34 Second group of patient preparation rooms

The invention claimed is:

1. A radiation assembly, comprising:
a radiation device comprising an accelerator, and a radiation projector; and
a radiation device gantry, wherein the gantry moveable supports the accelerator and projector, such that the accelerator and the projector can in unison be rotated about a horizontal patient treatment axis,
wherein the gantry provides a range of movement of the radiation device that defines a cylindrical treatment space, extending between a first end and a second opposite end, the cylindrical treatment space having the patient treatment axis at a centre thereof,
wherein the gantry comprises a first slew bearing at the first end of the cylindrical treatment space and a second slew bearing at the second end of the cylindrical treatment space to moveably support the radiation device, the slew bearings each having a central rotational axis that is aligned with the patient treatment axis, and
wherein at least one of the first slew bearing and the second slew bearing has a central opening that defines a treatment space entry port for moving a patient into and out of the treatment space.

2. The radiation assembly according to claim 1, wherein the gantry comprises a treatment housing that at least partially encloses the treatment space, the treatment housing being supported at opposite ends by the first slew bearing and the second slew bearing, and wherein the radiation device is mounted on the treatment housing, such that by rotating the treatment housing about the treatment axis, the radiation device is rotated about the treatment axis, and
wherein the gantry further supports a radiation device counterweight, and the radiation device counterweight is supported diametrically opposite to the radiation device, relative to the patient treatment axis.

3. A radiation facility comprising:
a radiation assembly comprising:
a radiation device comprising an accelerator, and a radiation projector; and
a radiation device gantry, wherein the gantry moveable supports the accelerator and projector, such that the accelerator and the projector can in unison be rotated about a horizontal patient treatment axis,
wherein the gantry provides a range of movement of the radiation device that defines a cylindrical treatment space that is dimensioned for receiving a patient, the treatment space extending between a first end and a second opposite end, the cylindrical treatment space having the patient treatment axis at a centre thereof, and
wherein the gantry comprises a first treatment space entry port at the first end of the of the cylindrical treatment space and a second treatment space entry port at the second end of the cylindrical treatment space,
a gantry track;
multiple patient preparation rooms, each for preparing a patient for treatment, wherein the multiple patient preparation rooms are set up in a first row of patient preparation rooms along a first side of the gantry track and a second row of patient preparation rooms along a second side of the gantry track,
wherein each of the patient preparation rooms is provided with a patient transfer port, wherein the patient transfer port faces the gantry track; and
a gantry manipulator, configured to move the radiation device gantry with the cylindrical treatment space along the gantry track and to position the radiation device gantry in a treatment position relative to each one of the multiple patient preparation rooms, in which treatment position, the first treatment space entry port the gantry is aligned with, and is adjacent to, the patient transfer port of the one of the multiple patient preparation rooms of the first row of patient preparation rooms and/or the second treatment space entry port is aligned with, and is adjacent to, the patient transfer port of the one of the multiple patient preparation rooms of the second row of patient preparation rooms, to enable a direct transfer of a patient, through the patient transfer port of the respective patient preparation room and through the respective first treatment space entry port or second treatment space entry port aligned with, and adjacent to, the patient transfer port, into the cylindrical treatment space of the radiation assembly and between the first treatment space entry port and the second treatment space entry port.

4. The radiation facility according to claim 3, wherein the gantry manipulator comprises:
a gantry carriage for transporting the gantry over the gantry track along the multiple preparation rooms; and
a drive for moving the gantry carriage along the gantry track,
wherein the gantry carriage has a carriage body that extends along a longitudinal axis, the longitudinal axis extending between a first end and an opposite second end, and wherein the patient treatment axis extends parallel to the longitudinal axis of the carriage body, and
wherein the carriage is at each end guided by the gantry track.

5. The radiation facility according to claim 4, wherein the gantry track is a transport track, the transport track extending along the multiple preparation rooms, wherein the multiple preparation rooms are stacked next to each other along the transport track, and
wherein the gantry carriage is supported by the transport track, for moving the gantry in a horizontal direction along the transport track and the multiple preparation rooms.

6. The radiation facility according to claim 5, wherein the gantry track and the gantry carriage are dimensioned such that the when the carriage supports the treatment space with one end in a treatment position relative to a first patient preparation room, the opposite end of the treatment space is supported in a treatment position relative to a second patient preparation room.

7. The radiation facility according to claim 5, wherein the multiple preparation rooms are set up with the patient transfer port facing a centre of the transport track, wherein the transport track comprises a circular circumferential guide rail, and the gantry carriage is at each end supported by the circumferential guide rail.

8. The radiation facility according claim 7, wherein the gantry track and the gantry carriage are dimensioned such that when the carriage supports the treatment space with one end in a treatment position relative to a first patient preparation room, the opposite end of the treatment space is supported in a treatment position relative to a second patient preparation room.

9. The radiation facility according to claim 4, wherein the gantry track comprises a horizontal transport track and a vertical lift track, and wherein one track is moveably supported by the other track, and the gantry carriage is coupled with the moveable supported track, to enable movement of the gantry along an array of preparation rooms.

10. The radiation facility according to claim 9, wherein the gantry track and the gantry carriage are dimensioned such that the when the carriage supports the treatment space with one end in a treatment position relative to a first patient preparation room, the opposite end of the treatment space is supported in a treatment position relative to a second patient preparation room.

11. The radiation facility according to claim 3, wherein the gantry manipulator further comprises a gantry housing, the gantry housing enclosing the gantry, and being configured to move with the gantry, to contain radiation emitted by the radiation device.

12. A method for moving the gantry of the radiation facility according to claim 3 from a first treatment position adjacent a first preparation room of the radiation facility to a second treatment position adjacent a second preparation room of the radiation facility, the method comprising using the gantry manipulator of the radiation facility according to claim 3 to effectuate said moving of the gantry.

13. A radiation facility comprising:
a radiation assembly comprising:
a radiation device comprising an accelerator, and a radiation projector; and
a radiation device gantry, wherein the gantry moveable supports the accelerator and the radiation projector, such that the accelerator and the projector can in unison be rotated about a horizontal patient treatment axis,
wherein the gantry provides a range of movement of the radiation device that defines a cylindrical treatment space, that is dimensioned for receiving a patient, the treatment space extending between a first end and a second opposite end, the cylindrical treatment space having the patient treatment axis at a centre thereof, and
wherein the gantry comprises a first treatment space entry port at the first end of the of the cylindrical treatment space and a second treatment space entry port at the second end of the cylindrical treatment space;
multiple patient preparation rooms, each for preparing a patient for treatment and each provided with a patient transfer port,
wherein a first group of the multiple patient preparation rooms is located on a first patient preparation room track at a side of the radiation device gantry with the first treatment space entry port and a second group of the multiple patient preparation rooms is located on a second patient preparation room track at a side of the radiation device gantry with the second treatment space entry port, and wherein the patient transfer port of each of the patient preparation rooms on the first patient preparation room track faces the second patient preparation room track and vice versa;
a first patient preparation room manipulator that is configured to move the patient preparation rooms of the first group along the first patient preparation room track and to position each of the patient preparation rooms of the first group in a treatment position, in which treatment position the first treatment space entry port is aligned with the patient transfer port of one of the patient preparation rooms of the first group, to enable direct transfer of a patient from the preparation room into the treatment space; and
a second patient preparation room manipulator that is configured to move the patient preparation rooms of the second group along the second patient preparation room track and to position each of the patient preparation rooms of the second group in a treatment position, in which treatment position the second treatment space entry port is aligned with the patient transfer port of one of the patient preparation rooms of the second group, to enable direct transfer of a patient from the preparation room into the treatment space.

14. The radiation facility according to claim 13, wherein the first and second patient preparation room manipulators each comprises:

a patient preparation room carriage for transporting the multiple patient preparation rooms over the patient preparation room track along the gantry; and a drive for moving the patient preparation room carriage along the patient preparation room track.

15. The radiation facility according to claim 14, wherein the patient preparation room tracks are transport tracks, the transport tracks extending along the gantry, wherein the multiple preparation rooms are stacked next to each other along the transport tracks, and wherein the patient preparation room carriages are supported by the transport tracks, for moving the patient preparation rooms in a horizontal direction along the transport tracks and the gantry.

16. A method for moving a patient support table from one of the preparation rooms into the treatment space of the gantry of the radiation facility according to claim 13, the method comprising:

moving the preparation room in the treatment position wherein the preparation room is adjacent to the gantry using the patient preparation room manipulator; and moving the patient support table via the treatment space entry port into the treatment space.

17. A method for moving a patient support table from one of multiple preparation rooms into a cylindrical treatment space of a radiation device gantry of a radiation facility, wherein the radiation facility comprises:

a radiation assembly comprising:

a radiation device comprising an accelerator and a radiation projector; and the radiation device gantry, wherein the gantry moveable supports the accelerator and the radiation projector, such that the accelerator and the radiation projector can in unison be rotated about a horizontal patient treatment axis, wherein the gantry provides a range of movement of the radiation device that defines the cylindrical treatment space, extending between a first end and a second opposite end, the cylindrical treatment space having the patient treatment axis at a centre thereof, and wherein the gantry comprises a first treatment space entry port at the first end of the of the cylindrical treatment space and a second treatment space entry port at the second end of the cylindrical treatment space;

the multiple patient preparation rooms, provided at both ends of the cylindrical treatment space;

each for preparing a patient for treatment, each of the preparation rooms being provided with a patient transfer port; and a patient preparation room manipulator, configured to position the multiple patient preparation rooms in a treatment position, in which treatment position, at least one of the first and second treatment space entry ports of the gantry is aligned with the patient transfer port of one of the patient preparation rooms, to enable direct transfer of a patient, through the patient transfer port and through the first or second treatment space entry port, from one of the preparation rooms into the treatment space for treatment of the patient in the treatment space of the radiation assembly, the method comprising:

using the first patient preparation manipulator to move the preparation room of the first group into the treatment position at the first end of the gantry, in which treatment position the preparation room is adjacent to the gantry;

moving the patient support table from a first preparation room of the second group of preparation rooms, the first preparation room being located in the treatment position at the second end of the gantry, out of the treatment space via the treatment space entry port at the second end of the gantry;

moving the patient support table of the preparation room of the first group into the treatment space via the treatment space entry port at the first end of the gantry; and using the second patient preparation manipulator to move the first preparation room out of the treatment position and to simultaneously move a second preparation room of the second group into the treatment position at the second end of the gantry.

* * * * *